(12) United States Patent
Kast et al.

(10) Patent No.: US 8,123,567 B2
(45) Date of Patent: Feb. 28, 2012

(54) CONNECTOR ASSEMBLIES AND CONTACTS FOR IMPLANTABLE MEDICAL ELECTRICAL SYSTEMS

(75) Inventors: John E. Kast, Hugo, MN (US); Charles E. Peters, Blaine, MN (US); Michael J. Baade, Zimmerman, MN (US); James A. Alexander, Shorewood, MN (US); Andrew J. Ries, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 12/680,603

(22) PCT Filed: Sep. 24, 2008

(86) PCT No.: PCT/US2008/077483
§ 371 (c)(1),
(2), (4) Date: Aug. 20, 2010

(87) PCT Pub. No.: WO2009/045809
PCT Pub. Date: Apr. 9, 2009

(65) Prior Publication Data
US 2010/0304592 A1    Dec. 2, 2010

(51) Int. Cl.
*H01R 24/04* (2006.01)
(52) U.S. Cl. .................... 439/668; 439/857
(58) Field of Classification Search .............. 439/668, 439/669, 909, 830, 816, 857, 856; 607/37, 607/36
See application file for complete search history.

(56) References Cited

U.S. PATENT DOCUMENTS

| | | | |
|---|---|---|---|
| 4,469,104 A | 9/1984 | Peers-Trevarton | |
| 4,712,557 A | 12/1987 | Harris | |
| 4,869,255 A | 9/1989 | Putz | |
| 5,046,242 A | 9/1991 | Kuzma | |
| 5,076,270 A * | 12/1991 | Stutz, Jr. | 607/37 |
| 5,336,246 A * | 8/1994 | Dantanarayana | 607/37 |
| 5,354,326 A | 10/1994 | Comben et al. | |
| 5,560,358 A | 10/1996 | Arnold et al. | |
| 5,947,761 A | 9/1999 | Pepe | |
| 6,064,509 A * | 5/2000 | Tonar et al. | 359/272 |
| 6,162,101 A | 12/2000 | Fischer et al. | |
| 6,321,126 B1 | 11/2001 | Kuzma | |
| 6,415,168 B1 | 7/2002 | Putz | |
| 6,575,793 B1 | 6/2003 | Li et al. | |
| 6,662,035 B2 | 12/2003 | Sochor | |
| 6,671,534 B2 | 12/2003 | Putz | |
| 6,725,096 B2 | 4/2004 | Chinn et al. | |
| 6,741,892 B1 | 5/2004 | Meadows et al. | |
| 6,776,635 B2 * | 8/2004 | Blanchfield et al. | 439/181 |
| 7,083,474 B1 * | 8/2006 | Fleck et al. | 439/668 |
| 7,134,919 B2 | 11/2006 | Putz | |
| 7,402,083 B2 | 7/2008 | Kast et al. | |
| 7,425,142 B1 | 9/2008 | Putz | |

(Continued)

FOREIGN PATENT DOCUMENTS
WO    WO98/48896    11/1998
(Continued)

*Primary Examiner* — Gary F. Paumen

(57) ABSTRACT

A connector assembly of a medical electrical device includes a plurality of electrical contacts, wherein at least one contact of the plurality of electrical contacts includes an electrical coupling receptacle. The electrical coupling receptacle of the at least one contact includes a first portion, which is adapted to receive a connector element of a medical electrical lead, and a second portion, in which a part of a feedthrough member extends, and to which the part of the feedthrough member is fixedly coupled.

37 Claims, 11 Drawing Sheets

U.S. PATENT DOCUMENTS

| | | | |
|---|---|---|---|
| 7,425,145 B2 * | 9/2008 | Ngo | 439/290 |
| 7,731,550 B2 * | 6/2010 | Falchetti | 439/857 |
| 7,798,862 B2 | 9/2010 | Kast et al. | |
| 7,892,050 B2 * | 2/2011 | Pavlovic et al. | 439/839 |
| 2003/0050549 A1 * | 3/2003 | Sochor | 600/378 |
| 2003/0069612 A1 * | 4/2003 | Zart et al. | 607/36 |
| 2003/0082958 A1 * | 5/2003 | Robinson et al. | 439/885 |
| 2003/0163171 A1 * | 8/2003 | Kast et al. | 607/36 |
| 2005/0033138 A1 * | 2/2005 | Ries et al. | 600/377 |
| 2005/0118887 A1 | 6/2005 | Hoffer et al. | |
| 2006/0167522 A1 | 7/2006 | Malinowski | |
| 2007/0239222 A1 * | 10/2007 | Sprain et al. | 607/37 |
| 2010/0240253 A1 | 9/2010 | Kast et al. | |

FOREIGN PATENT DOCUMENTS

WO  WO2007/109762  9/2007

* cited by examiner

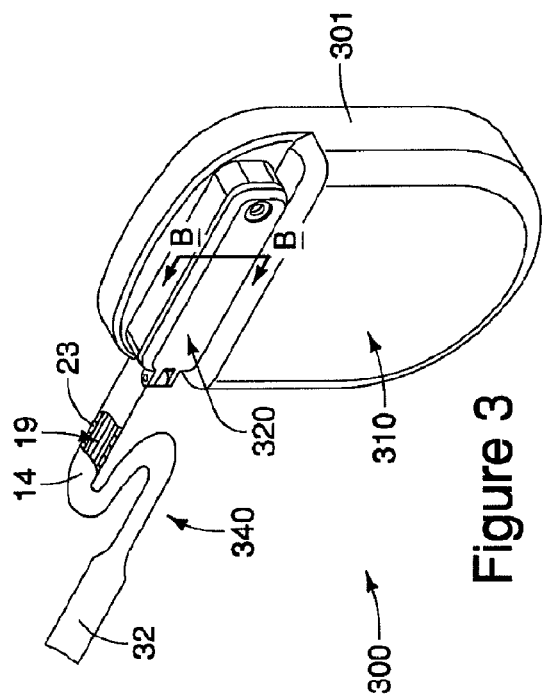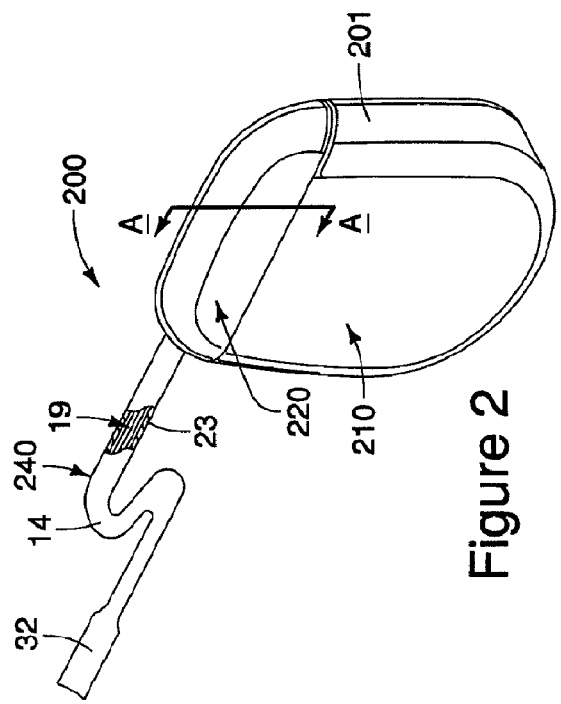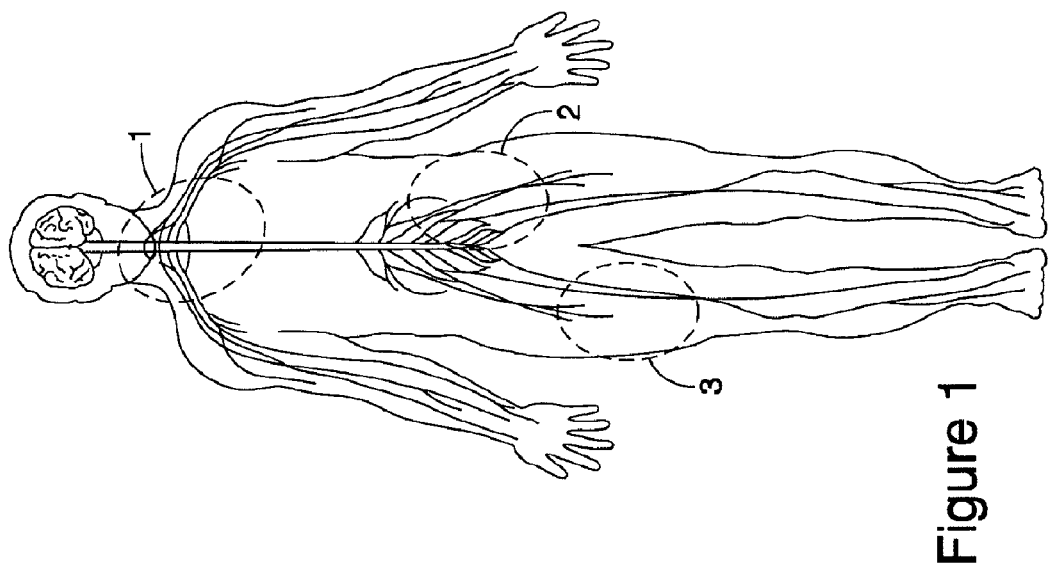

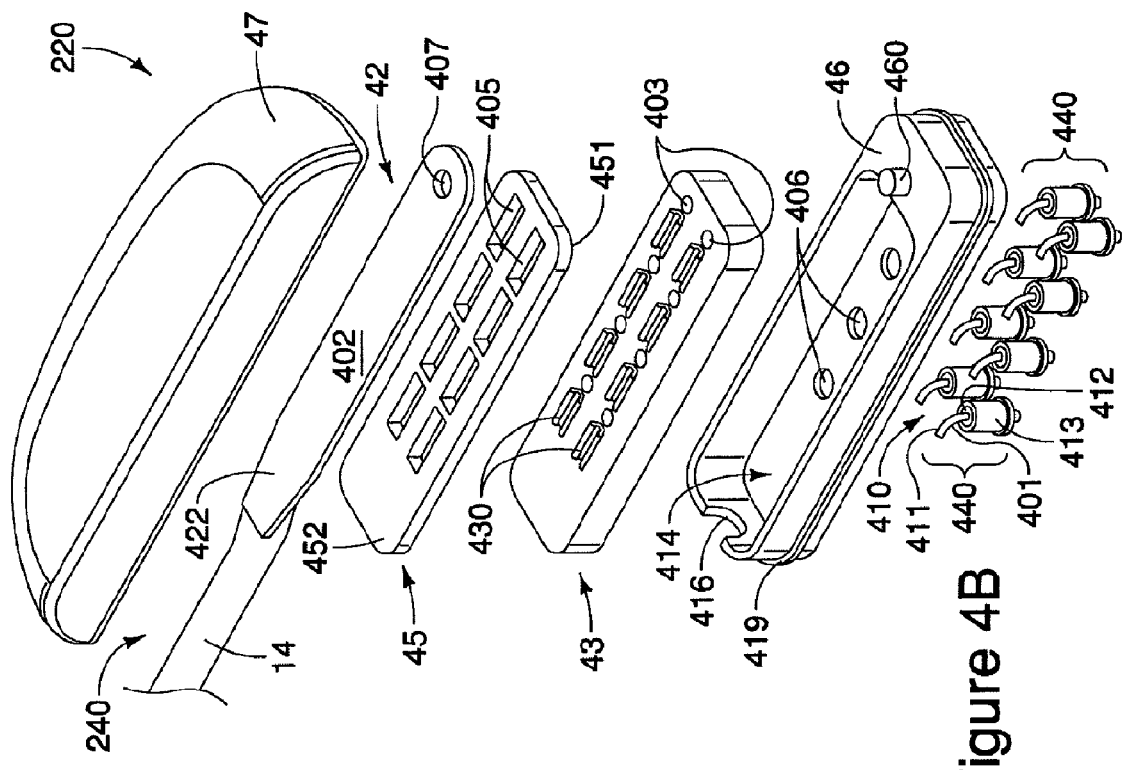
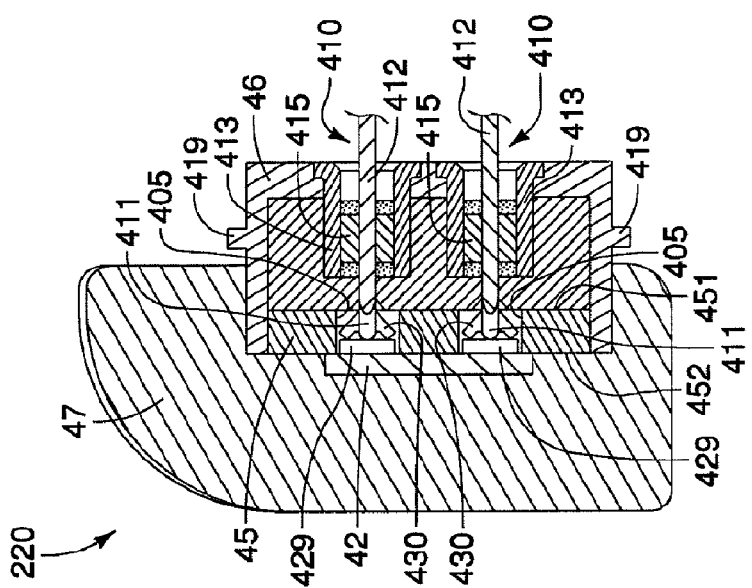
Figure 4B
Figure 4A

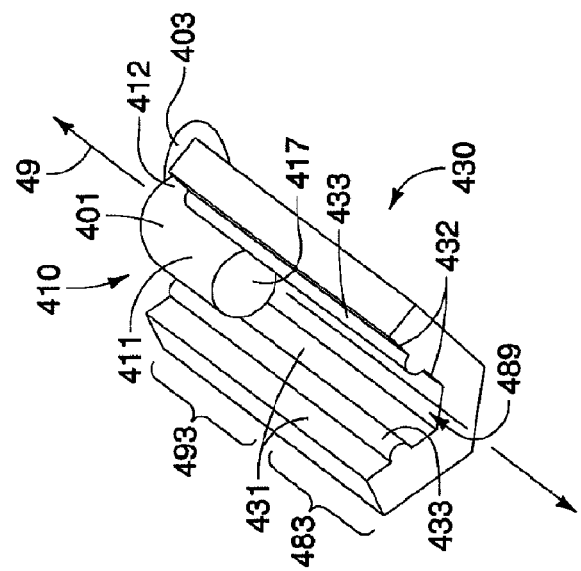
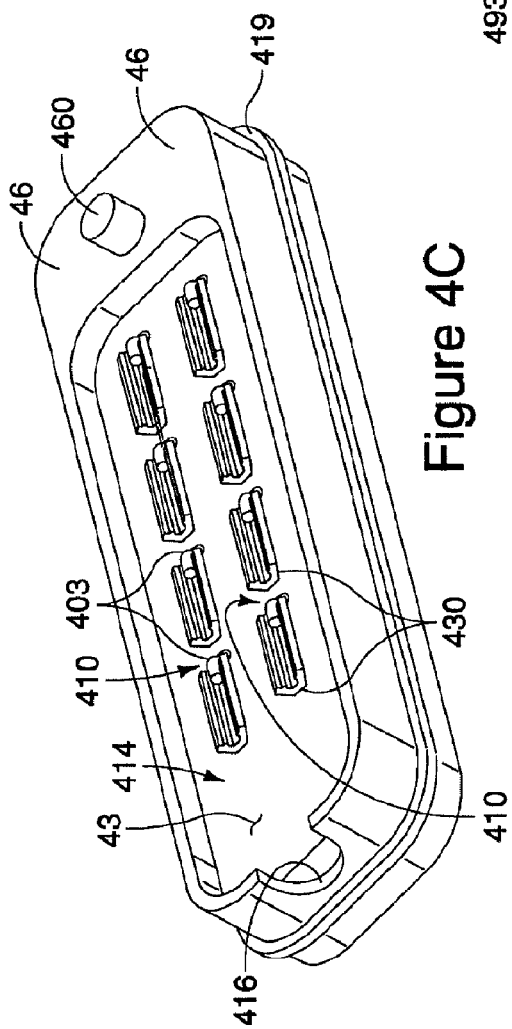
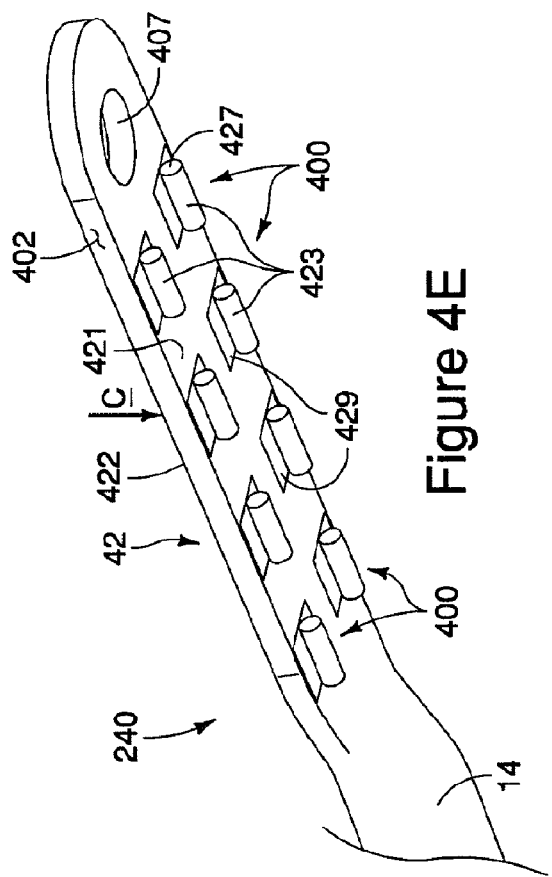
Figure 4C
Figure 4D
Figure 4E

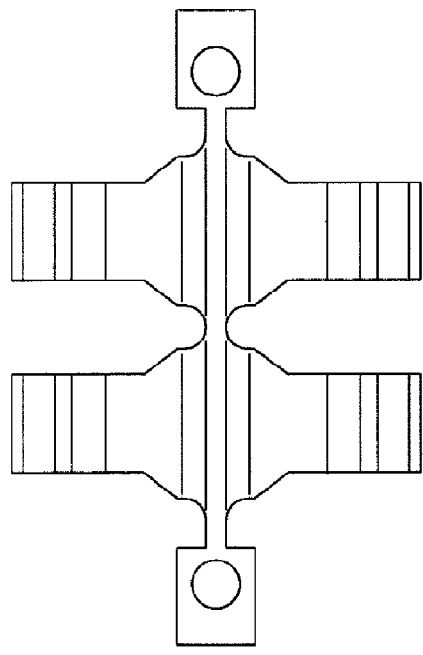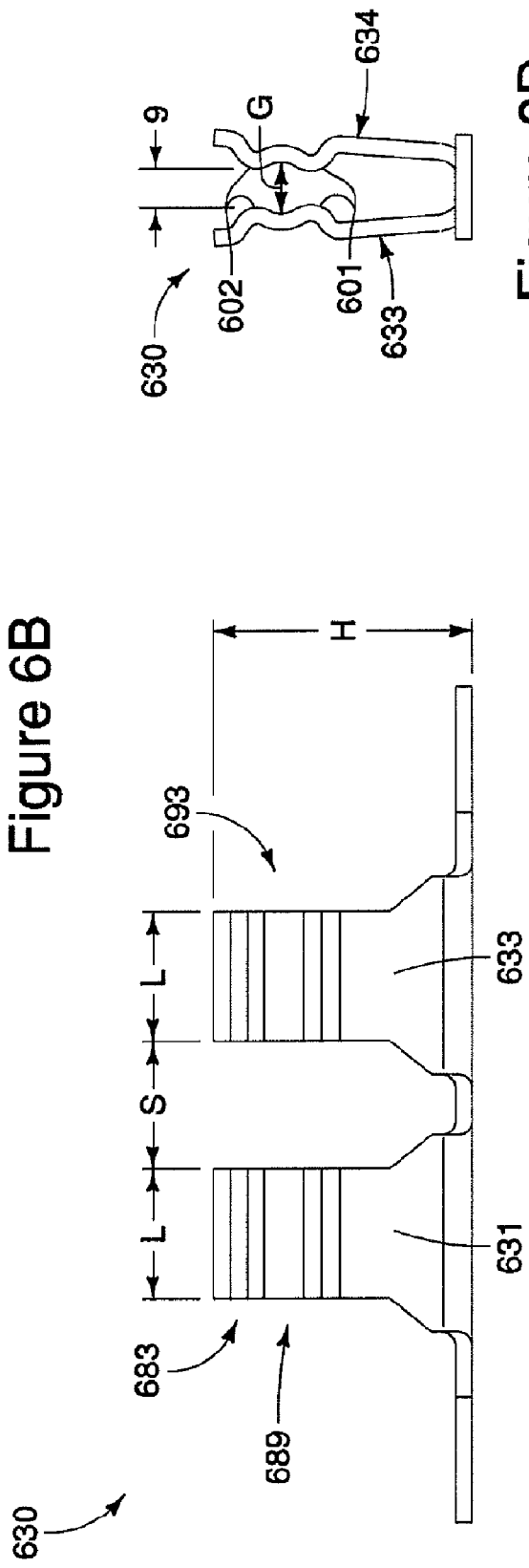

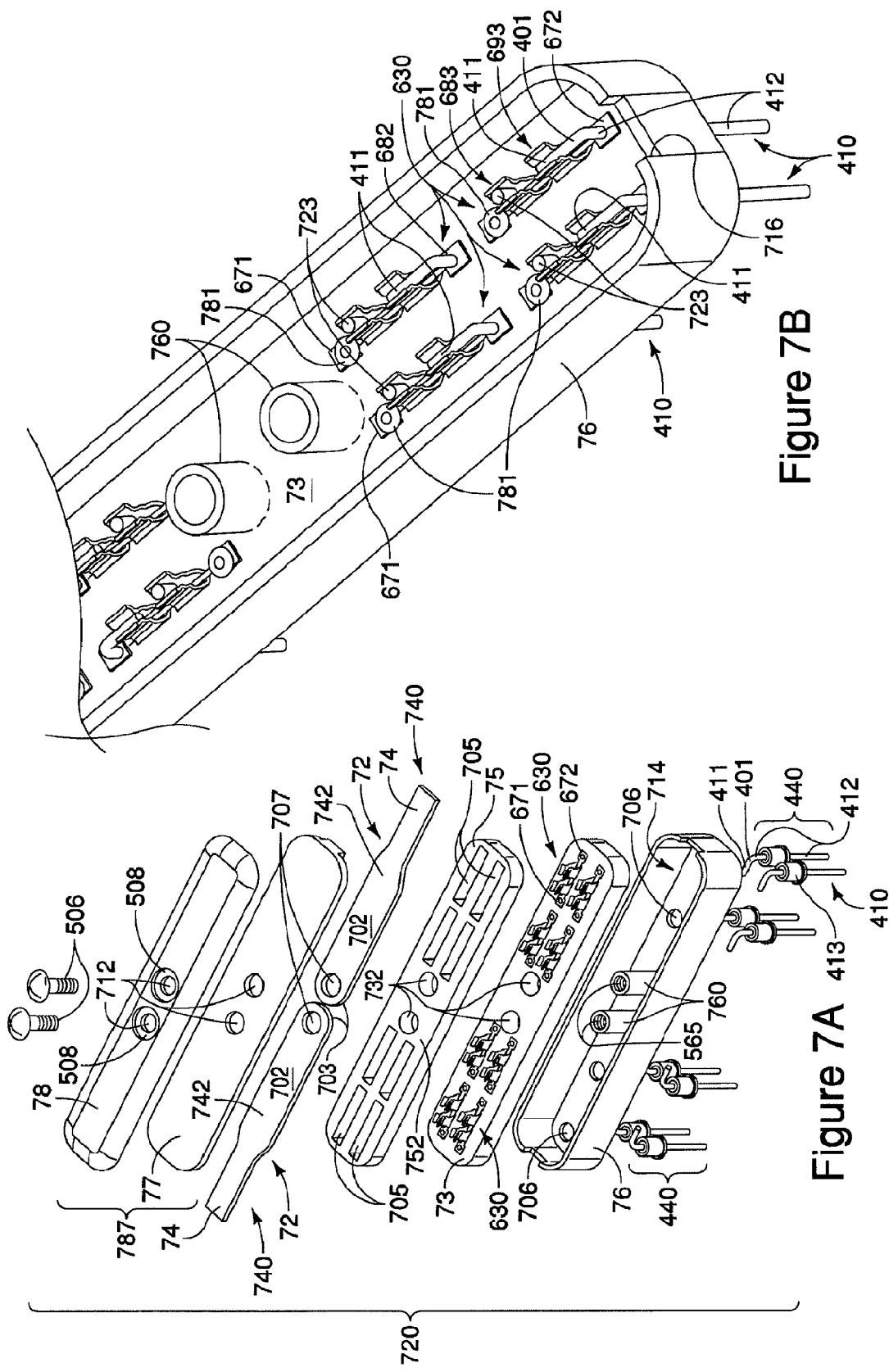

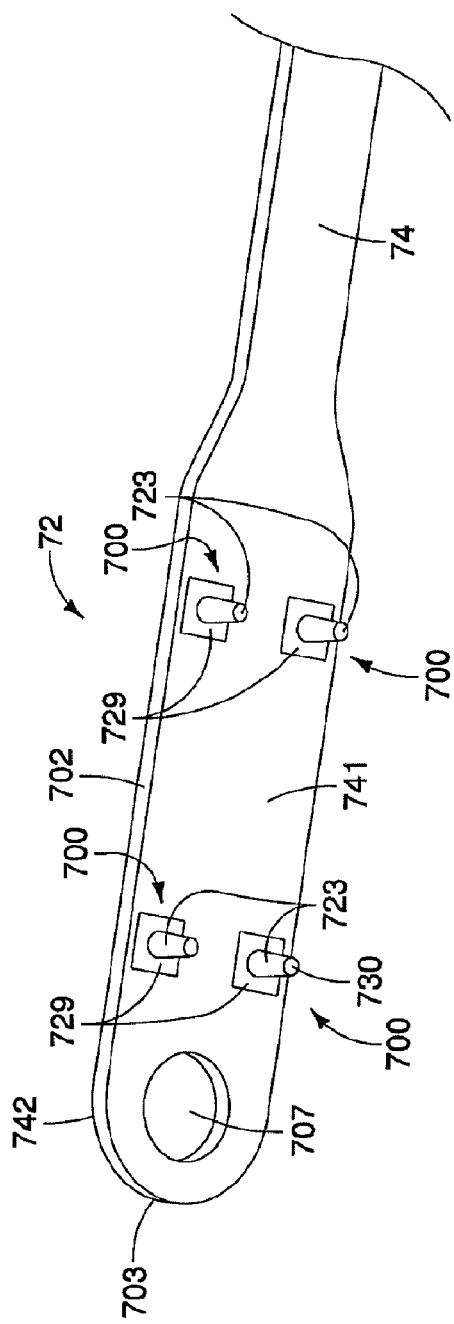
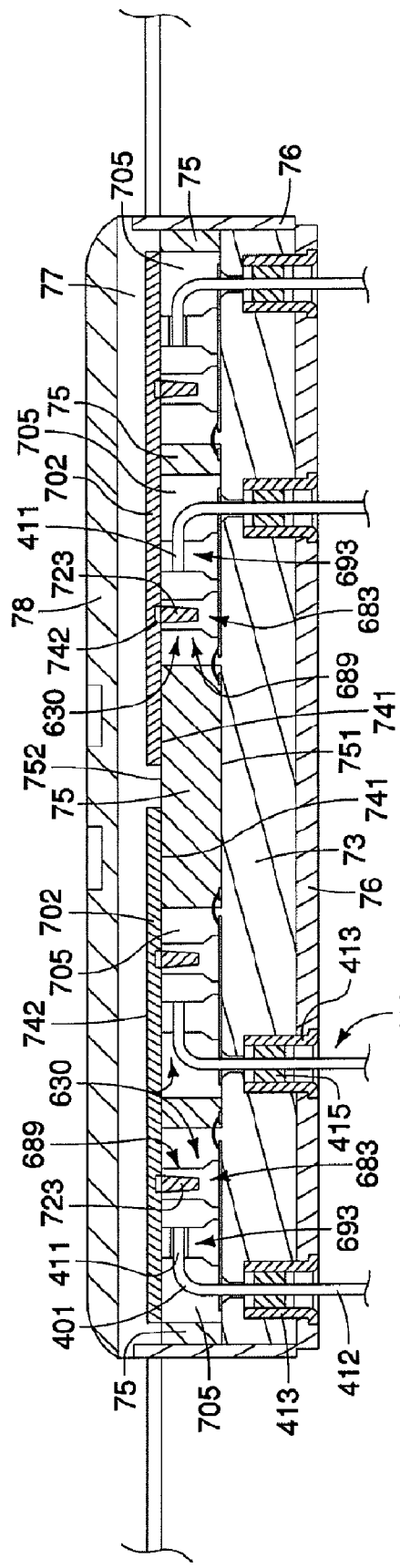
Figure 7C
Figure 7D

US 8,123,567 B2

CONNECTOR ASSEMBLIES AND CONTACTS FOR IMPLANTABLE MEDICAL ELECTRICAL SYSTEMS

This application is a U.S. National Stage filing under 35 U.S.C. 371 of copending PCT Application Serial No. PCT/US2008/077483, filed Sep. 24, 2008, which claims the benefit of U.S. Provisional Application No. 60/976,864, filed Oct. 2, 2007, "Connector Assemblies and Contacts for Implantable Medical Electrical Systems", the disclosure of all of the above which are incorporated by reference herein in its entirety.

TECHNICAL FIELD

The present disclosure pertains to implantable medical electrical devices and systems, and more particularly to connector assemblies and electrical contacts employed by the devices and systems.

BACKGROUND

Implantable neuromodulation systems can provide electrical stimulation for the treatment of pain and/or various neurological disorders. Neuromodulation systems typically include a plurality of stimulation electrodes which may be implanted at specific sites along a spinal cord, a peripheral nerve, or in a brain of a patient; the plurality of electrodes are typically mounted to an elongate lead body which carries corresponding conductors for electrical coupling of the electrodes to a neuromodulation device. Electrical coupling to the device is accomplished via connector elements terminating each conductor at a lead connector, which is configured to mate with a corresponding connector port of the neuromodulation device.

In recent years, new models of neuromodulation systems have been developed for increased functionality, for example, in providing stimulation from an increasing number of lead electrodes. In order to accommodate the increased functionality, while keeping a bulk of these implantable systems to a minimum, for patient comfort, there is a need for miniaturization of system components and higher density arrangements of these components without sacrificing system reliability.

BRIEF DESCRIPTION OF THE DRAWINGS

The following drawings are illustrative of particular exemplary embodiments and therefore do not limit the scope of the invention. The drawings are not to scale (unless so stated) and are intended for use in conjunction with the explanations in the following detailed description. Disclosed embodiments will hereinafter be described in conjunction with the appended drawings, wherein like numerals denote like elements.

FIG. 1 is a schematic of a human body showing various general implant locations for implantable neuromodulation systems.

FIG. 2 is a portion of an exemplary neuromodulation system, according to some embodiments of a first group of embodiments.

FIG. 3 is a portion of an exemplary neuromodulation system, according to some embodiments of a second group of embodiments.

FIG. 4A is a cross-section view of a device connector assembly, through section line A-A of FIG. 2, according to some embodiments.

FIG. 4B is an exploded perspective view of the connector assembly shown in FIG. 4A.

FIG. 4C is a perspective view of a portion of the connector assembly shown in FIGS. 4A-B.

FIG. 4D is a detailed perspective view of an electrical contact from the assembly shown in FIGS. 4A-C, according to some embodiments.

FIG. 4E is a perspective view of a medical electrical lead connector portion of the system shown in FIG. 2, according to some embodiments.

FIG. 6B is a plan view of a sheet metal piece from which the contact shown in FIG. 6A may be formed.

FIG. 6C is an elevation view of the contact shown in FIG. 6A.

FIG. 6D is an end view of the contact shown in FIG. 6A.

FIG. 7A is an exploded perspective view of a device connector assembly and portions of a pair of medical electrical leads, according to some alternate embodiments in a third group of embodiments.

FIG. 7B is a detailed perspective view of a portion of the connector assembly shown in FIG. 7A.

FIG. 7C is a perspective view of a medical electrical lead connector, according to some alternate embodiments.

FIG. 7D is a longitudinal section view through the device connector assembly of FIGS. 7A-B.

DETAILED DESCRIPTION

Figure 4F:
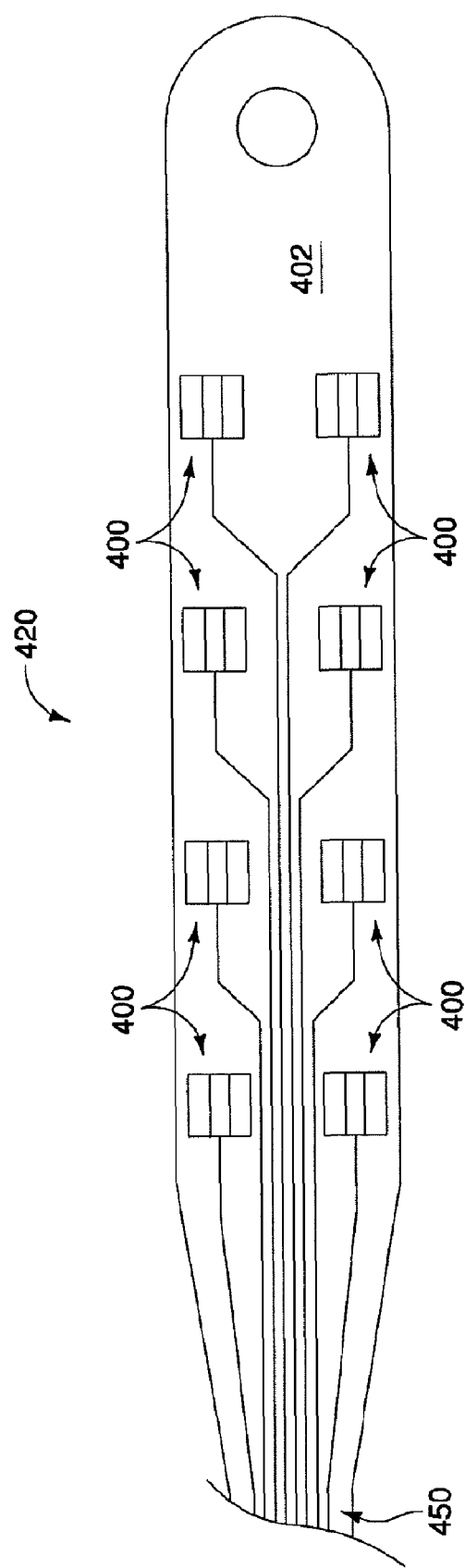
FIG. 4F is a schematic representative of conductor routing for the lead connector portion shown in 4E, according to some embodiments.

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

FIG. 1 is a schematic plan view of a human body showing various general implant locations 1, 2, 3 for portions of implantable neuromodulation systems; and FIGS. 2 and 3 are perspective views of portions of neuromodulation systems 200, 300 according to two groups of embodiments. FIG. 1 illustrates location 1 encompassing a pectoral region and a neck region, which extends behind the ears, around the base of the skull, and within which a pocket may be formed for a neuromodulation device, for example one of devices 210, 310, from which a lead may extend for stimulation of peripheral nerves, either within or adjacent the region, or for deep brain stimulation. FIG. 1 illustrates location 2 encompassing an abdominal and buttock region, within which a pocket may be formed to hold a neuromodulation device, from which one or more leads may extend for stimulation of peripheral nerves, either within or adjacent the region, or for spinal cord simulation. FIG. 1 illustrates location 3 encompassing an upper thigh region, within which a pocket may be formed to hold a neuromodulation device, from which one or more leads may extend for stimulation of peripheral nerves, either within or adjacent to the region.

FIGS. 2 and 3 illustrate systems 200, 300 each including a medical electrical lead 240 and 340, respectively. According to the illustrated embodiments, leads 240 and 340 are extension leads for other medical electrical leads that include stimulation electrodes, which are not shown; however, it should be appreciated that, according to alternate embodiments, leads 240 and 340 themselves may extend over a longer length and include stimulation electrodes. The use of extension leads in neuromodulation systems is well known to those skilled in the art. FIGS. 2 and 3 further illustrate each device 210 and 310 including a connector assembly 220, 320, respectively, which is mounted to a housing 201, 301 of each device, and to which the corresponding lead 240, 340 is coupled, according to two groups of embodiments. Each of leads 240, 340 is shown including a distal connector port 32, for coupling with the other leads including electrodes, and a lead body 14 formed by an insulative sheath 23, for example, silicone rubber or polyurethane tubing, and a plurality of conductors 19, for example, MP35N alloy wires, either cabled or coiled, extending therein from the corresponding connector assembly 220, 320 to distal connector port 32. According to the embodiment illustrated in FIG. 2, lead 240 is fixedly coupled to connector assembly 220, while, according to the embodiment illustrated in FIG. 3, lead 340 is reversibly coupled to connector assembly 320.

FIG. 4A is a cross-section through section line A-A of FIG. 2; and FIG. 4B is an exploded perspective view of connector assembly 220. FIG. 4A illustrates a connector 42 of lead 240 enclosed within a top seal member 47 of connector assembly 220; top seal member 47 may be formed from silicone rubber or polyurethane. FIGS. 4A-B illustrate connector assembly 220 including a plurality of feedthrough assemblies 440, wherein each assembly 440 extends though a corresponding opening 406 of a feedthrough mount 46 to which a ferrule 413 of each feedthrough assembly 440 is joined, for example, via welding around openings 406. Those skilled in the art will appreciate that mount 46 is formed from any suitable biocompatible and biostable metal, for example, titanium, is mounted to an opening in housing 201 and may be welded thereto at a flange 419 of mount 46. FIGS. 4A-B further illustrate an insulative base 43, for example, formed from a thermoplastic such as PEEK or polysulfone, which is located within a cavity 414 of mount 46 and surrounds each feedthrough assembly 440; base 43 supports a plurality of electrical contacts 430, wherein each contact 430 is electrically coupled, via a corresponding feedthrough assembly 440, to electronic circuitry enclosed within housing 201 of device 210 (FIG. 2). According to the illustrated embodiment, assembly 220 further includes a sealing member 45, for example, formed from silicone rubber, having a first surface 451 mating with base 43, and a second surface 452 mating with top seal member 47 to electrically isolate each electrical coupling between connector 42 and contacts 430; sealing member 45 is shown including a plurality of apertures 405, wherein each contact 430 extends through a corresponding aperture 405 and is recessed with respect to second surface 452. First surface 451 of sealing member 45 may be adhesively bonded to base 43, for example, with silicone medical adhesive. According to some preferred methods, a siloxane coating is first applied, via a plasma treatment, to base 43, which base 43 is preferably formed from polysulfone, and then a pre-coat of silicone medical adhesive, which is thinned in heptane (i.e., approximately a 1:1 ratio) is applied to base 43 as a primer for the subsequent bonding of sealing member 45 thereto with the silicone medical adhesive.

Each feedthrough assembly 440 includes a feedthrough member 410 extending through ferrule 413 and surrounded by an insulator element 415, for example, a glass or ceramic, known to those skilled in the art, which is hermetically sealed, for example, via a braze joint, known to those skilled in the art, to feedthrough member 410 and to ferrule 413. Mount 46, ferrules 413 and feedthrough members 410 may each be formed from any suitable material, examples of which include, without limitation titanium, niobium, platinum, platinum/iridium, molybdenum, zirconium and tantalum. According to the illustrated embodiment, each feedthrough member 410 includes a first part 411, electrically coupled to the corresponding electrical contact 430, a second part 412, extending through a corresponding port 403 of insulative base 43 and away from the corresponding contact 430, for electrical coupling within housing 201, and a bend 401 located between first and second parts 411, 412.

FIG. 4C is a perspective view of a portion of connector assembly 220; FIG. 4D is a detailed perspective view featuring one of electrical contacts 430; and FIG. 4E is a perspective view of lead connector 42. FIG. 4C illustrates an arrangement of contacts 430 in two columns on base 43 within cavity 414, for example, having been coupled to base 43 via insert molding of base about contacts 430. FIG. 4D illustrates the electrical coupling of each first part 411 of feedthrough member 410 to the corresponding electrical contact 430. FIG. 4D further illustrates contact 430 including an elongate electrical coupling receptacle 489, which is formed by a groove extending approximately parallel with a longitudinal axis 49 of contact 430; coupling receptacle 489 has a first portion 483, adapted to receive a connector element 400 of lead connector 42 (FIG. 4E), and a second portion 493, in which first part 411 of feedthrough member 410 extends and to which first part 411 is fixedly coupled, for example, via welding. FIG. 4E illustrates connector elements 400 coupled to, and protruding from a first side 421 of an insulative substrate 402 of connector 42, and arranged in two columns for alignment and coupling with first portions 483 of electrical coupling receptacles 489; and FIG. 4C shows mount 46 including an optional post 460 for mating with an optional aperture 407 of connector 42, which may, in an initial assembly of connector 42, facilitate proper alignment of connector elements 400 with electrical coupling receptacles 489. FIGS. 4B-C further illustrate a relief or cut out portion 416 in mount 46 providing clearance and strain relief for lead body 14 of lead 240 at a transition area from connector 42.

According to the illustrated embodiment, each connector element 400 includes an approximately cylindrical portion 423 having a longitudinal axis extending approximately parallel to first side 421 of substrate 402, such that, when pressed into electrical coupling receptacle 489, for electrical coupling to the corresponding electrical contact 430, an end 427 of approximately cylindrical portion 423 is adjacent an end 417 of fixedly coupled feedthrough member 410. Each element 400 may be pressed into the corresponding electrical coupling receptacle 489 by applying a force, for example, per arrow C, to a second side 422 of substrate 402. FIG. 4D further illustrates electrical coupling receptacle 489 of contact 430 formed by first and second sidewalls 431, 432, which are opposite one another and extend at an angle away from one another; an elongate protrusion 433, for example having a radius of approximately 0.002 inch, is shown extending longitudinally along each sidewall 431, 432. Protrusions 433 create a 'snap fit' for insertion of connector elements 400 into electrical coupling receptacle 489 and provide an additional retaining force to secure both connector element 400 and feedthrough member 410 within electrical coupling receptacle 489. It should be noted that alternate embodiments of the present invention need not include protrusions 433 to create such a 'snap fit'. Furthermore, alternate groove contours may be employed by contacts 430 according to alternate embodiments. Configurations of alternate electrical contact embodiments will be described below, in conjunction with FIGS. 6, 7B and 7D. Connector elements 400 and contacts 430 may be formed from any suitable conductive material, examples of which include, without limitation, gold, platinum/iridium, tantalum, titanium, MP35N alloy, and stainless steel. According to some embodiments, a diameter of cylindrical portion 423 is approximately equal to a diameter of first part 411 of feedthrough member 410, which diameter may be in a range from approximately 0.005 inch to approximately 0.010 inch.

A first force may be applied to press portions 423 of connector elements 400 past protrusions 433 and into electrical coupling receptacles 489 of contacts 430 for electrical coupling, and a subsequent second, and opposite, force may be applied to lift connector elements 400 out from electrical coupling receptacles 489. Each of these forces could adversely load feedthrough assemblies 440, for example, at interfaces of insulator elements 415, were it not for bend 401 formed in each feedthrough member 410 between first and second parts 411, 412 thereof.

FIG. 4E further illustrates each connector element 400 further including a flange 429 extending laterally from the corresponding cylindrical portion 423. According to some preferred embodiments, flanges 429 are embedded in substrate 402, for example, via injection molding, to secure each connector element 400 to connector 42. If insulative substrate 402 of connector 42 is relatively flexible, for example, being formed from silicone rubber or polyurethane, flanges 429, being formed from any of the aforementioned relatively rigid and conductive materials, or from a relatively rigid plastic, may lend stability to inserting each cylindrical portion 423 into first portion 483 of electrical coupling receptacle 489, for example, by pressing, per arrow C, against second side 422 of substrate 402. Although FIGS. 4B and 4E illustrate substrate 402 having approximately planar surfaces, it should be understood that these surfaces may be deformable and/or include recessed or protruding features creating a non-planar contour, according to alternate embodiments.

FIG. 4F is a schematic representative of conductor routing for lead connector 42, according to some embodiments. FIG. 4F illustrates a plurality of insulated conductors 450 extending within substrate 402; each of conductors 450 is shown coupled to a corresponding electrical contact 400. Each of conductors 450 may be formed from one or more wires, for example, made from MP35N alloy, which may be either cabled or coiled, and each of which may be individually insulated with a jacket of insulative material, for example, formed from polyimide, PTFE, or ETFE, although substrate 402 may provide the primary isolation between conductors 450 so that the insulative jackets are not necessary. Coupling of each of conductors 450 to the corresponding contact 400 may be accomplished by welding or crimping according to methods known to those skilled in the art.

As previously described, in conjunction with FIG. 2, lead connector 42 is fixedly secured within connector assembly 220, and, with reference back to FIG. 4B, a method for assembling connector 220 may be appreciated. Once each feedthrough assembly 440 has been joined to feedthrough mount 46, and mount 46 has been joined to housing 201 (FIG. 2), and once base 43 and sealing member 45, for example, being bonded together, are assembled into cavity 416 of mount 46, such that each feedthrough member 410 is coupled to the corresponding electrical contact 430, and each contact 430 is surrounded by sealing member 45, lead connector 42 may be coupled to assembly 220 by pressing each connector element 400 thereof into the corresponding electrical contact 430. Assembly 220 is completed by forming top seal member 47 thereover; top seal member 47 may either be independently formed as a piece part and attached to assembly 220, for example, via adhesive bonding, with silicone medical adhesive to lead connector 42 and sealing member 45, or may be over-molded. According to some alternate embodiments, top seal member 47 may be attached to lead connector 42, before connector 42 is coupled to assembly 220, or formed as an integral part of lead connector 42, for example, as an extension of substrate 402.

Some exemplary embodiments from another group of embodiments, which was introduced in conjunction with FIG. 3, will now be described in greater detail in conjunction with FIGS. 5A-E. These exemplary embodiments include connector assembly 320 and lead 340, wherein assembly 320 is adapted to allow lead 340 to be connected and disconnected therefrom.

Figures 5A, 5B:
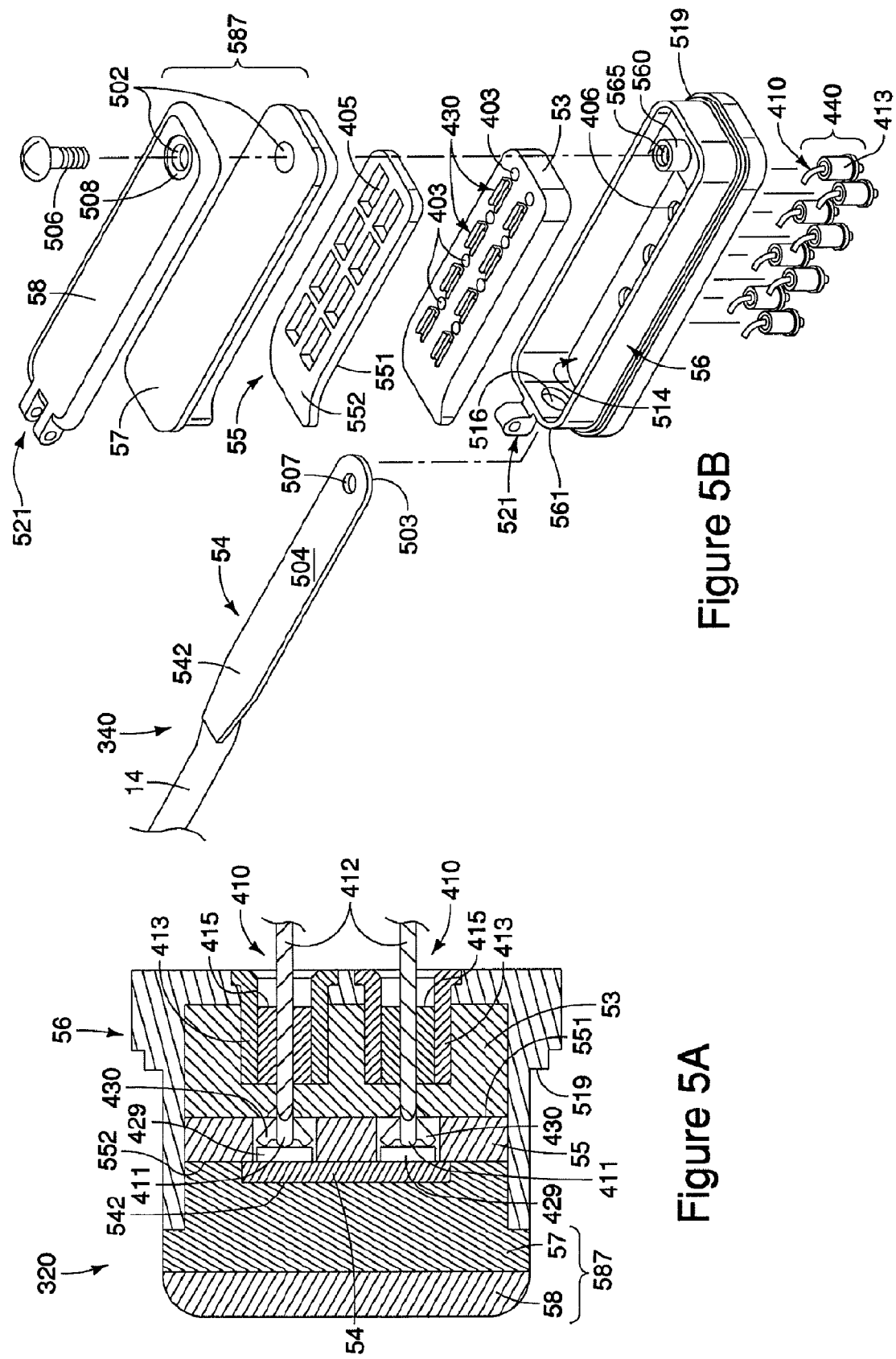
FIG. 5A is a cross-section view of a device connector assembly, through section line B-B of FIG. 3, according to some embodiments.
FIG. 5B is an exploded perspective view of the connector assembly shown in FIG. 5A.

FIG. 5A is a cross-section view of connector assembly 320, through section line B-B of FIG. 3, according to some embodiments; FIG. 5B is an exploded perspective view of connector assembly 320; and FIG. 5C is an elevation view of assembly 320, according to some embodiments. FIGS. 5A-C illustrate assembly 320 including a lid 587 that may be opened and closed, per arrow C, via a pivotable attachment 521 to a feedthrough mount 56 of assembly 320; lid 587 is shown including a relatively rigid outer member 58 and a relatively soft top seal member 57, for example, formed from silicone rubber, which may be attached thereto via a press fit. Outer member 58 of lid 587 may be formed from any relatively rigid biocompatible and biostable material, either plastic or metal. Feedthrough mount 56, like mount 46, previously described, is formed from any suitable biocompatible and biostable metal, for example, titanium, and is mounted to an opening in housing 301 (FIG. 3), for example, being welded thereto at a shoulder 519 of mount 56. FIG. 5B further illustrates lid 587 including an aperture 502 for mating about a post 560 of mount 56; an internal surface of post 560 may include threads 565 to receive a fastener 506, whose head may be tightened against a counter-bore 508 of rigid outer member 58 of lid 587 to secure lid 587 in a closed position. According to an alternate embodiment, aperture 502 and post 560 may include mating detent features for a snap fit to secure lid 587 in a closed position. FIG. 5A illustrates lid 587 in the closed position, and a connector 54 of lead 340 enclosed, sealed and secured within assembly 320 by lid 587, while FIG. 5C illustrates lid 587 in an open position.

Like connector assembly 220, previously described, connector assembly 320 includes the plurality of feedthrough assemblies 440, wherein each feedthrough assembly 440 extends through a corresponding opening 406 of mount 56, and each feedthrough assembly 440 includes ferrule 413, joined to mount 56, feedthrough member 410, coupled to a corresponding electrical contact 430, and insulator element 415 hermetically sealed to ferrule 413 and feedthrough member 410. An insulative base 53 of connector assembly 320 supports contacts 430 and includes ports 403 to allow feedthrough members 410 to extend through base 53 for electrical coupling with contacts 430; the electrical coupling of feedthrough members 410 to contacts 430 may be the same as that described, in conjunction with FIG. 4D, for connector assembly 220.

FIGS. 5A-B further illustrate a sealing member 55, for example, formed from silicone rubber, of connector assembly 320 including apertures 405 extending therethrough from a first surface 551 to a second surface 552 thereof, such that sealing member 55, when joined along first surface 551 to base 53, surrounds each contact 430 to help isolate each electrical coupling between connector 54 and contacts 430. Sealing member 55 may be joined to base 53 via adhesive bonding, for example, according to the method previously described for assembly 220, in conjunction with FIGS. 4A-B. With reference to FIG. 5A, in conjunction with FIG. 5D, contacts 430 may be seen recessed, with respect to second surface 552 of sealing member 55, within apertures 405; and, with reference to FIG. 5E, connector 54 may be seen including connector elements 400, which protrude from a first side 541 of an insulative substrate 504 of connector 54, in a similar manner as for lead connector 42 (FIG. 4E), so that each connector element 400 of lead connector 54 may be pressed into first portion 483 of electrical coupling receptacle 489 of the corresponding contact 430 for electrical coupling in a similar fashion to that described for connector 42 and assembly 220, for example, by applying a force along a second side 542 of substrate 504. Once coupled, lid 587 is closed over connector 54, and, with reference to FIG. 5A, it may be appreciated that top seal member 57 of lid 587 mates with second side 542 of insulative substrate 504 of connector 54 as well as with second surface 552 of sealing member 55 in order to complete the isolation of each electrical coupling between connector 54 and contacts 430.

Figure 5D:
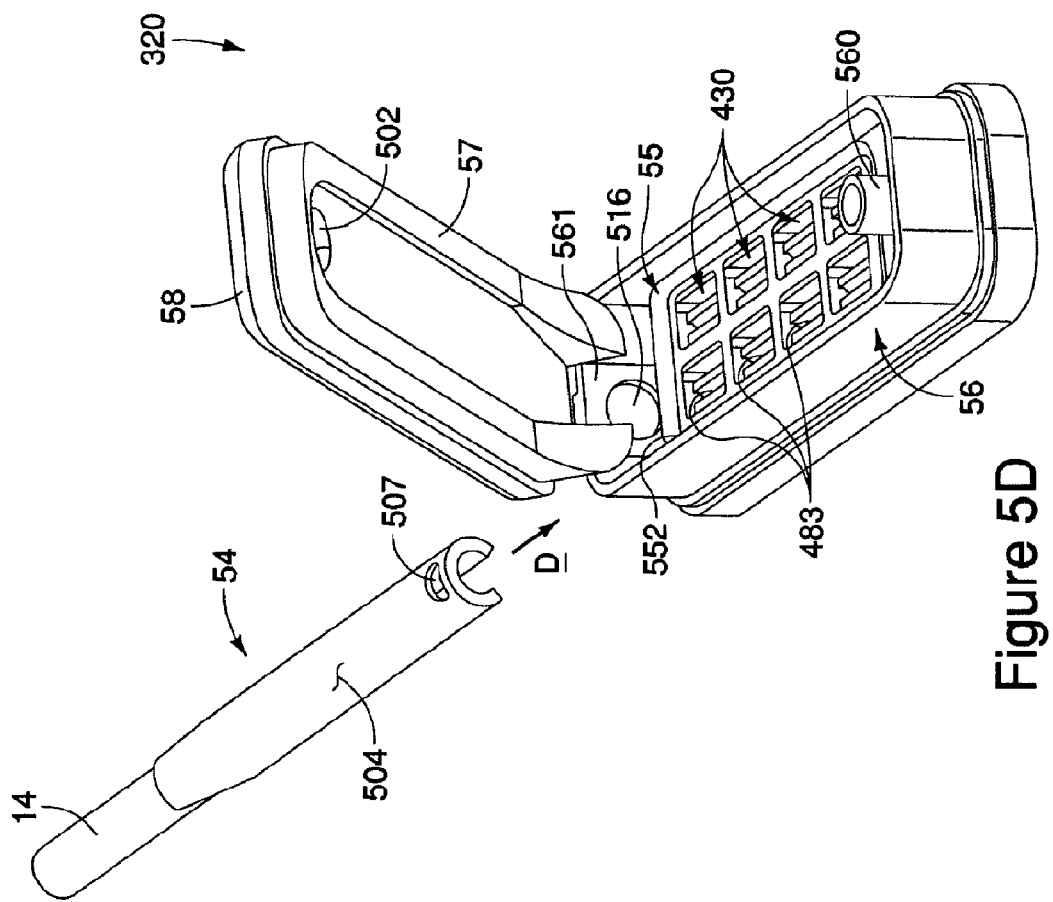
FIG. 5D is a perspective view of a lead connector positioned and configured for insertion into the connector assembly shown in FIGS. 5A-C.
Figure 5C:
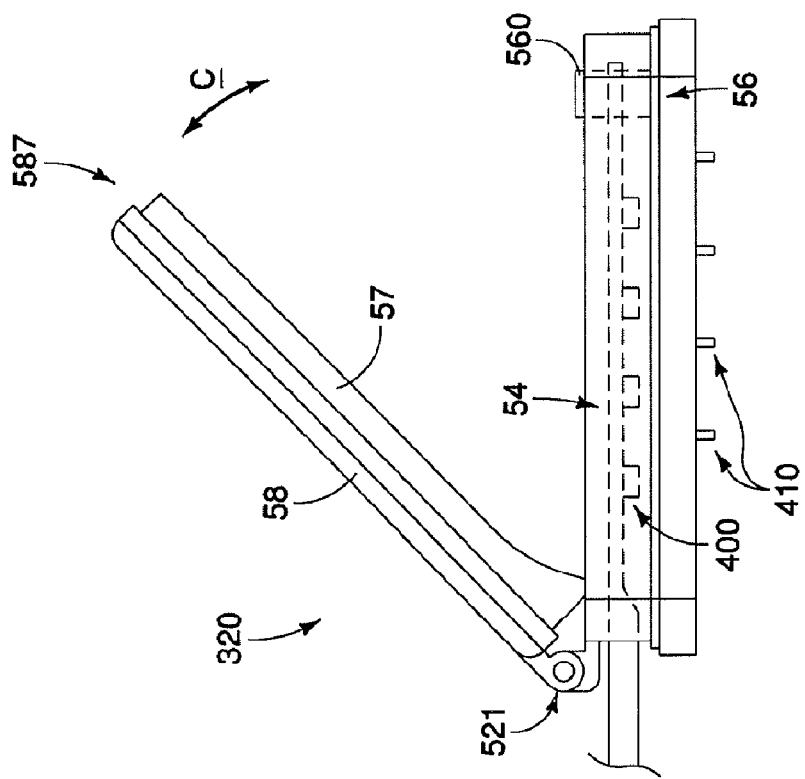
FIG. 5C is an elevation view of the connector assembly shown in FIGS. 5A-B, according to some embodiments.
Figure 5E:
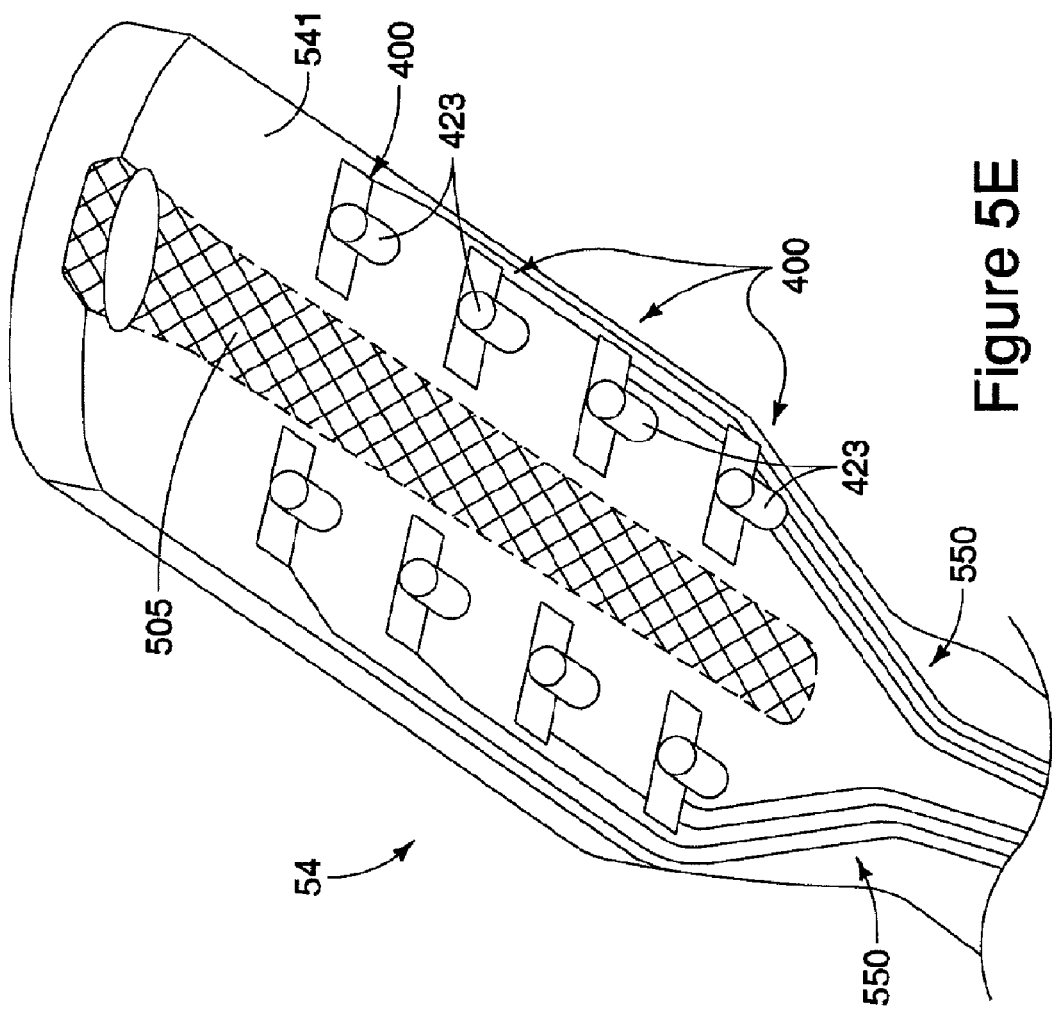
FIG. 5E is a schematic representation of conductor routing for the lead connector shown in FIG. 5D, according to some embodiments.

With further reference to FIG. 5D, lead connector 54 is shown positioned for insertion, per arrow D, into assembly 320, via an insertion port 516 extending through a relatively rigid sidewall 561 of feedthrough mount 56; insulative substrate 504 of lead connector 54 is shown deformed to fit through insertion port 516. According to the illustrated embodiment, substrate 504 is formed from a flexible material, for example, silicone rubber or polyurethane, and, with further reference to FIG. 5E, a schematic representation of conductor routing for connector 54, according to some embodiments, shows conductors 550 of lead connector 54 routed away from connector elements 400 so as not to cross over a folding or bending zone 505 of substrate 504. FIG. 5E further illustrates bending zone 505 as an area of substrate 504, which has a reduced wall thickness to facilitate the bending, according to some embodiments. Once connector 54 has been inserted through port 516, substrate 504 may be opened up into a more planar configuration, for example, as illustrated in FIGS. 5A-B and 5E, and as represented with dashed lines in FIG. 5C, for alignment of connector elements 400 over electrical contacts 430 of assembly 320. According to alternate embodiments, a cross-sectional area of insertion port 516 is sized to allow passage of connector 54 therethrough without deformation of substrate 504.

FIGS. 5B and 5D further illustrate connector 54 including an alignment aperture 507 extending through substrate 504, in proximity to a proximal end 503 of connector 54, which aperture 507, once connector 54 has been inserted through port 516, may be mated with post 560 of mount 56, as illustrated, with dashed lines, in FIG. 5C. Alignment aperture 507 may help to align each connector element 400 with electrical coupling receptacle first portion 483 of the corresponding contact 430, thereby facilitating proper coupling of connector 54 within connector assembly 320. With reference to FIGS. 5C-D, it may be appreciated that a location, adjacent to insertion port 516, of pivotable attachment 521 for lid 587, provides for a lifting of lid 587 in a direction that leaves ample clearance for grasping of connector 54, once connector is inserted through port 516, in order to properly align connector 54 over electrical contacts 430, whose electrical coupling receptacles 489 are exposed by opened lid 587. The location of pivotable attachment 521 also provides for clearance to press connector 54 against contacts 430, in order to insert each connector element 400 into first portion 483 of electrical coupling receptacle 489 of the corresponding electrical contact 430. After connector 54 is fully inserted for electrical coupling, lid 587 may be closed and secured over connector 54 as previously described. If and when device 310 (FIG. 3) needs to be exchanged for a new device, lid 587 may be re-opened to expose lead connector 54 for disconnection therefrom; to disconnect connector 54, a portion of substrate 504, that is adjacent to proximal end 503, may be lifted away from, or 'peeled' back from, contacts 430 in order to separate each connector element 400 out from electrical coupling receptacle 489 of the corresponding electrical contact 430.

Figure 6A:
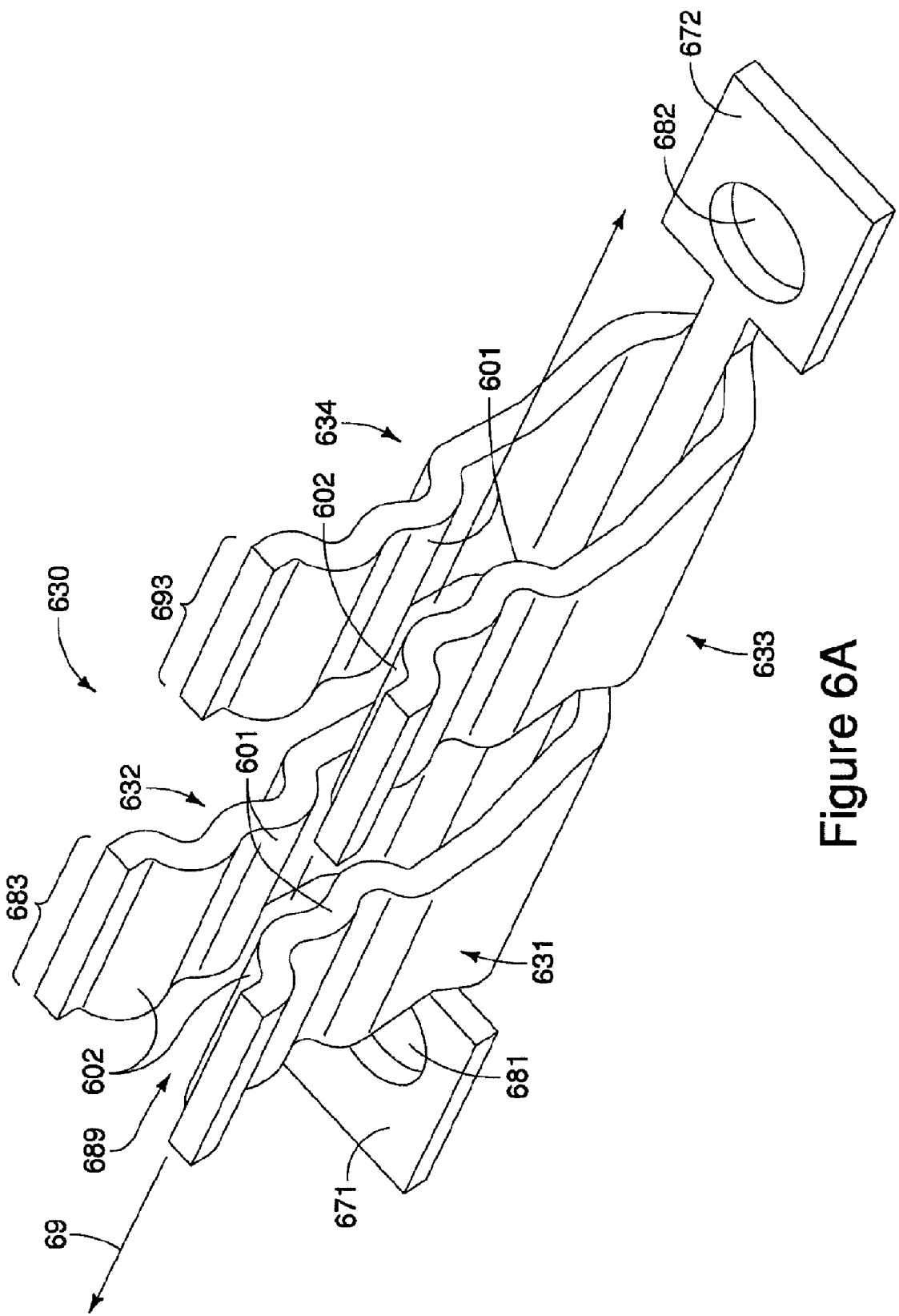
FIG. 6A is a perspective view of an electrical contact, according to some alternate embodiments.

Turning now to FIGS. 6A-D, an electrical contact 630, according to some alternate embodiments, is shown. Contact 630 may be incorporated as a substitute for any or all of contacts 430, within either of the previously described connector assemblies 220, 320, being supported by base 43, 53, respectively. FIGS. 6A-D illustrate electrical contact 630 including an elongate electrical coupling receptacle 689; coupling receptacle 689 includes a first portion 683 and a second portion 693, each of which portions 683.693 extends approximately parallel with a longitudinal axis 69 of contact 630. FIG. 6A further illustrates first portion 683 formed by first and second opposing sidewalls 631 and 632, respectively, and second portion 693 likewise formed by third and fourth opposing sidewalls 633 and 634, respectively. Each sidewall 631, 632, 633, 634 is shown including first and second protrusions 601, 602, which extend within coupling receptacle 689 and are offset from one another in a direction approximately orthogonal to longitudinal axis 69. According to the illustrated embodiment, one of first and second portions 683, 693 may receive a connector element of a lead connector, for example, connector element 400 of either of lead connectors 42, 54 (FIGS. 4E, 5E), and the other first and second portions 683, 693 may receive a feedthrough member, for example, first part 411 of feedthrough member 410, fixedly coupled thereto.

With further reference to FIG. 6A, electrical contact 630 also includes first and second tabs 671, 672, in which first and second openings 681, 682, respectively, are formed. According to the illustrated embodiment, the one of first and second openings 681, 682, which is adjacent to that portion, 683 or 693, to which feedthrough member 410 is fixedly coupled, may be aligned with one of ports 403 of either of insulative bases 43, 53 to allow passage of second part 412 of feedthrough member 410 therethrough (FIGS. 4B and 5B). The other of first and second openings 681, 682 may then be used for securing contact 630 to either of bases 43, 53, for example, via a fastening element 781 extending therethrough, which will be described in more detail below, in conjunction with FIGS. 7A-B.

According to exemplary embodiments, contact 630 is made from MP35N sheet metal, which has a thickness of approximately 0.0025 inch and has been stamped, or otherwise formed, into the shape shown in FIG. 6B. Referring now to FIGS. 6C-D, which are an elevation and an end view, respectively, of contact 630, some exemplary dimensions of contact 630 will be defined. With reference to FIG. 6C a spacing S between first portion 683 and second portion 693 of coupling receptacle 689 may be approximately 0.02 inch, a length L of each portion 683, 693 may also be approximately 0.02 inch, and an overall height H of contact 630 may be approximately 0.04 inch. With reference to FIG. 6D, a minimum relaxed gap g between sidewall 631 and sidewall 632, and between sidewall 633 and sidewall 634, for example, between opposing protrusions 602, may be approximately 0.0060 inches, while a relaxed gap G, between each of the aforementioned opposing sidewalls, in between protrusions 601 and 602 may be approximately 0.0077 inch.

FIG. 7A is an exploded perspective view of a device connector assembly 720, which may be mounted to a device housing, for example, housing 310, in a manner similar to that described for connector assemblies 220 and 320 (FIGS. 2, 3, 4A and 5A); and FIG. 7B is a detailed perspective view of a portion of assembly 720. Device connector assembly 720 is representative of alternate exemplary embodiments in which either of contacts 430, 630 may be incorporated, although FIGS. 7A-B show contacts 630 incorporated therein. FIGS. 7A-B illustrate connector assembly 720 including a feedthrough mount 76, which has a cavity 714 for holding an insulative base 73, and a plurality of feedthrough assemblies 440, as previously described, wherein each feedthrough assembly 440 extends though a corresponding opening 706 of feedthrough mount 76; those skilled in the art will appreciate that mount 76 is formed from any suitable biocompatible and biostable metal, for example, titanium. Feedthrough member 410, of each feedthrough assembly 440, extends through a corresponding port (not shown) of insulative base 73 and through second opening 682 of the corresponding electrical contact 630, which is supported by base 73, to be fixedly coupled, for example, via laser welding, within second portion 693 of contact coupling receptacle 689. FIG. 7B further illustrates each of fastening elements 781 extending through a corresponding tab 671, via openings 681 (FIG. 6), in order to secure contacts 630 to base 73. According to an exemplary embodiment, fastening elements 781 are formed from protruding posts, which may be integral with base 73; after opening 681 of tab 671 of each contact 630 is inserted around the corresponding post, a riveting operation, for example, either carried out ultrasonically or mechanically, deforms each post to form the illustrated fastening elements 781. According to alternate embodiments, pre-formed fastening elements 781, as individual components, may be inserted through apertures 681 and into base 73 after each contact is positioned on base 73. Opening 681 may have a diameter between approximately 0.005 inch and approximately 0.015 inch, preferably about 0.010 inch; thus, it may be appreciated that, due to the small size, in addition to an indexing advantage, posts which are integral with base 73 for forming fastening elements 781, for example, via riveting, would be preferred over insertion of individual pre-formed fastening elements 781.

Although not shown in FIG. 7B, it may be appreciated, with reference to FIGS. 7A and 7D, that a sealing member 75 of connector assembly 720 also fits within cavity 714 of mount 76 and includes apertures 705 in order to surround each contact 630 to help isolate contacts 630 from one another in a manner similar to that previously shown and described for device connector assemblies 220 and 320. Sealing member 75 may be formed from silicone rubber and base 73 from either polysulfone or PEEK, and sealing member 75 and base 73 may be adhesively bonded to one another via the method previously described in conjunction with FIGS. 4A-B.

FIG. 7A illustrates portions of two medical electrical leads 740, whose connectors 72 are positioned for coupling within connector assembly 720, and connector assembly 720 further including a lid 787 for securing the coupling. Each lead connector 72 is shown extending proximally from a lead body 74, which, although not shown, may extend distally to terminate in a connector port or in an electrode array, as previously described for leads 240 and 340, respectively. Lid 787 is shown including a relatively rigid outer member 78, for example, formed from any suitable biocompatible and biostable metal or plastic, and a relatively soft seal member 77, for example, formed from silicone rubber, to seal against a second side 742 of an insulative substrate 702 of each lead connector 72, when connector 72 is coupled within device connector assembly 720. Seal member 77 may be attached to outer member 78, for example, via a press fit. FIG. 7A further illustrates lid 787 including a pair of apertures 712 for mating about a pair of posts 760 that extend upward from mount 76 through apertures 732 of both base 73 and sealing member 75; an internal surface of each post 760 may include threads 565 to receive a corresponding fastener 506, whose head may be tightened against a corresponding counter-bore 508 of rigid outer member 78 of lid 787 in order to secure lid 787 over lead connectors 72.

FIG. 7C is a perspective view of one of lead connectors 72; and FIG. 7D is a longitudinal section view through a column of contacts 630 in device connector assembly 720, wherein lead connectors 72 are enclosed, sealed and secured for electrical coupling with contacts 630. FIG. 7C illustrates insulative substrate 702 of connector 72 having a first side 741 from which a plurality of connector elements 700 protrude; each connector element 700 includes an approximately cylindrical portion 723 and a flange 729 extending laterally therefrom and being embedded in insulative substrate 702. According to the illustrated embodiment, a longitudinal axis of each approximately cylindrical portion 723 extends in a direction approximately orthogonal to first side 741 insulative substrate 702, and each connector element 700 of lead connector 72 may be pressed into first portion 683 of electrical coupling receptacle 689 of the corresponding contact 630 for electrical coupling as illustrated in FIG. 7D. With reference to FIG. 7D, in conjunction with FIG. 7A, it may be appreciated that contacts 630, which extend within apertures 705 of sealing member 75, are recessed below second surface 752 thereof, such that, when connector elements 700 are coupled in coupling receptacles 789 and top seal member 77 of lid 787 is secured against second side 742 of connector substrate 702, first side 741 of connector substrate 702 seals against second surface 752 of sealing member 75. Lead connector elements 700, in their entirety or just portions 723 thereof, and device electrical contacts 630 may be formed from any suitable conductive material, examples of which include, without limitation, gold, platinum/iridium, tantalum, titanium, MP35N alloy, and stainless steel. If insulative substrate 702 of connector 72 is relatively flexible, for example, being formed from silicone rubber or polyurethane, flanges 729, being formed from any of the aforementioned relatively rigid and conductive materials, or from a relatively rigid plastic, may lend stability to inserting each cylindrical portion 723 into first portion 683 of electrical coupling receptacle 689, for example, by pressing against second side 742 of substrate 702.

With reference back to FIG. 6A, in conjunction with FIGS. 7B and 7D, it may be appreciated that two pair of opposing contact surfaces are formed, for coupling with approximately cylindrical portions 723 of connector elements 700, by first and second protrusions 601, 602 of each of first and second sidewalls 631, 632 forming first portion 683 of coupling receptacle 689. With further reference to FIG. 7C, it may be noted that, according to some preferred embodiments, approximately cylindrical portions are slightly tapered from flange 729 to a terminal end 730, which may facilitate insertion thereof into coupling receptacle 689. According to some embodiments, a diameter of cylindrical portion 723 is in a range from approximately 0.005 inch to approximately 0.012 inch. With further reference to FIG. 6, in conjunction with FIGS. 7B and 7D, first part 411 of each feedthrough member 410 is shown inserted between protrusions 601 and 602 of opposing sidewalls 633, 634 for coupling within second portion 693 of electrical coupling receptacle 689 of the corresponding contact 630. According to some embodiments, a diameter of at least first part 411 of feedthrough member 410 is in a range from approximately 0.005 inch to approximately 0.012 inch.

FIGS. 7A and 7C further illustrate each connector 72 including an alignment aperture 707 extending through substrate 702, in proximity to a proximal end 703 of each connector 72; each aperture 707 may be mated with one of posts 760 of mount 76 in order to help to align each connector element 700 with electrical coupling receptacle first portion 683 of the corresponding contact 630, thereby facilitating proper coupling of connectors 72 within connector assembly 720, for example, as is illustrated in the section view of FIG. 7D. The plurality of contacts 630 are shown divided into two groups of four of contacts 630, wherein the two groups are arranged as a mirror image of one another, about posts 760, in order to accommodate the illustrated end-to-end placement of lead connectors 72. However, it should be noted that alternate embodiments of the present invention are not limited to such an arrangement.

In the foregoing detailed description, the invention has been described with reference to specific embodiments. However, it may be appreciated that various modifications and changes can be made without departing from the scope of the invention as set forth in the appended claims.

We claim:

1. A medical electrical device comprising a housing, electronic circuitry enclosed within the housing, and a connector assembly mounted on the housing, the connector assembly comprising:
a plurality of electrical contacts, at least one electrical contact of the plurality of electrical contacts including a longitudinal axis and an elongate electrical coupling receptacle including a first portion and a second portion, each of the first and second portions extending approximately parallel to the longitudinal axis, and the first portion adapted to receive a connector element mounted on a connector of a medical electrical lead; and
a feedthrough member including a first part extending within the second portion of the electrical coupling receptacle of the at least one electrical contact and being fixedly coupled thereto, and a second part extending away from the electrical contact.

2. The device of claim 1, wherein the at least one contact of the plurality of electrical contacts further includes a first sidewall and a second sidewall, opposite the first sidewall, the first and second sidewalls extending at an angle away from one another to form the electrical coupling receptacle of the at least one electrical contact.

3. The device of claim 1, wherein the feedthrough member includes a bend located between the first and second parts thereof.

4. The device of claim 1, wherein:
the first portion of the electrical coupling receptacle of the at least one electrical contact is formed by first and second opposing sidewalls;
the second portion of the electrical coupling receptacle of the at least one electrical contact is formed by third and fourth opposing sidewalls; and
the first and second sidewalls are spaced apart from the third and fourth sidewalls along the longitudinal axis.

5. The device of claim 1, wherein the at least one electrical contact further includes a tab extending approximately parallel to the longitudinal axis, the tab including an opening through which the second part of the feedthrough member extends.

6. The device of claim 1, wherein:
the connector assembly further comprises an insulative base and a fastening element, the base extending between the plurality of electrical contacts and the housing, and the fastening element securing the at least one electrical contact to the base; and
the at least one electrical contact further includes a tab extending approximately parallel to the longitudinal axis, the tab including an opening through which the fastening element extends.

7. The device of claim 1, wherein:
the connector assembly further comprises an insulative base and a fastening element, the base extending between the plurality of electrical contacts and the housing, and the fastening element securing the at least one electrical contact to the base;
the at least one electrical contact further includes first and second tabs, each of the first and second tabs extending approximately parallel to the longitudinal axis;
the first tab includes an opening through which the fastening element extends; and
the second tab includes an opening through which the second part of the feedthrough member extends.

8. The device of claim 1, wherein:
the first portion of the electrical coupling receptacle of the at least one electrical contact includes a first pair of opposing contact surfaces and a second pair of opposing contact surfaces, the first pair of opposing contact surfaces being offset from the second pair of opposing contact surfaces in a direction approximately orthogonal to the longitudinal axis; and
the first and second pairs of opposing contact surfaces are adapted to couple with the connector element of the plurality of connector elements mounted on the medical electrical lead connector, when the connector element is received in the first portion.

9. The device of claim 1, wherein:
the second portion of the electrical coupling receptacle of the at least one electrical contact is formed by opposing sidewalls;
each of the opposing sidewalls includes a first protrusion and a second protrusion, each of the first and second protrusions extending within the coupling receptacle of the at least one electrical contact and being offset from one another in a direction approximately orthogonal to the longitudinal axis; and
the first part of the feedthrough member is fixedly coupled to the second portion of the electrical coupling receptacle of the at least one electrical contact between the first and second protrusions of the opposing sidewalls.

10. The device of claim 1, wherein:
the connector assembly further comprises a sealing member;
the sealing member includes an aperture; and
the at least one electrical contact extends within the aperture of the sealing member.

11. The device of claim 1, wherein the connector assembly further comprises an alignment feature for coupling with a mating feature of the connector of the lead in order to align at least one connector element of the plurality of connector elements with the first portion of the electrical coupling receptacle of the at least one electrical contact.

12. A medical electrical system comprising a medical electrical lead including a plurality of conductors, and a plurality of connector elements, each connector element of the plurality of connector elements being coupled to a corresponding conductor of the plurality of conductors, and a medical electrical device including a housing and a connector assembly mounted thereon, the connector assembly comprising:
a plurality of electrical contacts, at least one electrical contact of the plurality of electrical contacts including a longitudinal axis and an elongate electrical coupling receptacle including a first portion and a second portion, each of the first and second portions extending approximately parallel to the longitudinal axis, and the first portion adapted to receive a connector element of the plurality of connector elements of the lead; and
a feedthrough member including a first part extending within the second portion of the electrical coupling receptacle of the at least one electrical contact and being fixedly coupled thereto, and a second part extending away from the at least one electrical contact toward the housing.

13. The system of claim 12, wherein the connector element of the lead is fixedly coupled to the first portion of the electrical coupling receptacle of the at least one electrical contact.

14. The system of claim 12, wherein:
the connector assembly of the device further comprises an alignment feature; and
the medical electrical lead further includes a mating alignment feature for coupling with the alignment feature of the connector assembly of the device, in order to align the connector element of the lead with the first portion of the electrical coupling receptacle of the at least one electrical contact of the device connector assembly.

15. The system of claim 12, wherein the connector element of the lead connector includes an approximately cylindrical portion.

16. The system of claim 15, wherein:
the medical electrical lead further includes a connector on which the plurality of connector elements are mounted;
the lead connector includes an insulative substrate from which the connector element protrudes; and
the connector element further includes a flange extending laterally from the approximately cylindrical portion thereof, the flange being embedded in the insulative substrate of the lead connector.

17. The system of claim 15, wherein:
the medical electrical lead further includes a connector on which the plurality of connector elements are mounted; and
the lead connector includes an insulative substrate from which the connector element protrudes, such that a longitudinal axis of the approximately cylindrical portion of the connector element extends in a direction approximately parallel with the insulative substrate.

18. The system of claim 15, wherein:
the medical electrical lead further includes a connector on which the plurality of connector elements are mounted; and
the lead connector includes an insulative substrate from which the connector element protrudes, such that a longitudinal axis of the approximately cylindrical portion of the connector element extends in a direction approximately orthogonal to the insulative substrate.

19. The system of claim 12, wherein each feedthrough member of the device connector assembly includes a bend located between the first and second parts thereof.

20. The system of claim 12, wherein:
the device connector assembly further comprises a sealing member; and
wherein the sealing member includes an aperture; and
the at least one electrical contact of the device connector assembly extends within the aperture of the sealing member.

21. The system of claim 12, wherein the at least one electrical contact of the of the device connector assembly further includes a first sidewall and a second sidewall, opposite the first sidewall, the first and second sidewalls extending at an angle away from one another to form the electrical coupling receptacle of each electrical contact.

22. The system of claim 12, wherein:
the first portion of the electrical coupling receptacle of the at least one electrical contact of the device connector assembly is formed by first and second opposing sidewalls;
the second portion of the electrical coupling receptacle of the at least one electrical contact is formed by third and fourth opposing sidewalls; and
the first and second sidewalls are spaced apart from the third and fourth sidewalls along the longitudinal axis.

23. The system of claim 12, wherein the at least one electrical contact of the device connector assembly further includes a tab extending approximately parallel to the longitudinal axis, the tab including an opening through which the second part the feedthrough member extends.

24. The system of claim 12, wherein:
the at least one electrical contact of the device connector assembly further includes a tab extending approximately parallel to the longitudinal axis, the tab including an opening through which the second part the feedthrough member extends;
the device connector assembly further comprises an insulative base, the base extending between the at least one electrical contact of the device connector assembly and the housing; and
the base includes a port being aligned with the opening of the tab of the at least one electrical contact, such that the second part of the feedthrough member further extends through the port.

25. The system of claim 12, wherein:
the device connector assembly further comprises an insulative base and a fastening element, the base extending between the at least one electrical contact of the device connector assembly and the housing, and the fastening element securing the at least one electrical contact to the base; and
the at least one electrical contact of the device connector assembly further includes a tab extending approximately parallel to the longitudinal axis, the tab including an opening through which the fastening element extends.

26. The system of claim 12, wherein:
the device connector assembly further comprises an insulative base and a fastening element, the base extending between the at least one electrical contact of the device connector assembly and the housing, and the fastening element securing the at least one electrical contact to the base;
the at least one electrical contact of the device connector assembly further includes first and second tabs, each of the first and second tabs extending approximately parallel to the longitudinal axis;
the first tab including an opening through which the fastening element extends; and
the second tabs including an opening through which the second part of the feedthrough member extends.

27. The system of claim 12, wherein:
the first portion of the electrical coupling receptacle of the at least one electrical contact of the device connector assembly includes a first pair of opposing contact surfaces and a second pair of opposing contact surfaces, the first pair of opposing contact surfaces being offset from the second pair of opposing contact surfaces in a direction approximately orthogonal to the longitudinal axis; and
the first and second pairs of opposing contact surfaces are adapted to couple with the connector element mounted on the lead connector, when the connector element is received in the first portion.

28. The system of claim 12, wherein:
the second portion of the electrical coupling receptacle of the at least one electrical contact of the device connector assembly is formed by opposing sidewalls;
each of the opposing sidewalls includes a first protrusion and a second protrusion, each of the first and second protrusions extending within the coupling receptacle of the at least one electrical contact and being offset from one another in a direction approximately orthogonal to the longitudinal axis; and
the first part of the feedthrough member of the device connector assembly is fixedly coupled to the second portion of the electrical coupling receptacle of the at least one electrical contact between the first and second protrusions of the opposing sidewalls.

29. An electrical contact for a medical electrical device connector assembly, the contact comprising a longitudinal axis and an elongate electrical coupling receptacle, the electrical coupling receptacle including a first portion and a second portion, the first portion and the second portion extending approximately parallel to the longitudinal axis; the first portion being adapted to receive a single connector element of a plurality of connector elements mounted on a connector of a medical electrical lead; and the second portion adapted to receive a feedthrough member of the device; wherein:
the first portion of the electrical coupling receptacle includes a first pair of opposing contact surfaces and a second pair of opposing contact surfaces, the first pair of opposing contact surfaces being offset from the second pair of opposing contact surfaces in a direction approximately orthogonal to the longitudinal axis; and
the first and second pairs of opposing contact surfaces are adapted to couple with the connector element of the plurality of connector elements mounted on the medical electrical lead connector, when the connector element is received in the first portion.

30. The electrical contact of claim 29, wherein:
the first portion of the electrical coupling receptacle is formed by first and second opposing sidewalls;
the second portion of the electrical coupling receptacle is formed by third and fourth opposing sidewalls; and
the first and second sidewalls are spaced apart from the third and fourth sidewalls along the longitudinal axis.

31. An electrical contact for a medical electrical device connector assembly, the contact comprising a longitudinal axis, an elongate electrical coupling receptacle, and a tab; wherein:
the electrical coupling receptacle includes a first portion and a second portion, the first portion and the second portion extending approximately parallel to the longitudinal axis, the first portion adapted to receive a single connector element of a plurality of connector elements mounted on a connector of a medical electrical lead, and the second portion adapted to receive a feedthrough member of the device; and
the tab extends from the electrical coupling receptacle, approximately parallel to the longitudinal axis, the tab including an opening extending therethrough, the opening being sized and oriented to accommodate passage therethrough, from a side of the tab that faces away from the electrical coupling receptacle to a side of the tab that is adjacent the electrical coupling receptacle, an extension of the feedthrough member of the device, or a fastening element for attaching the contact to an insulative base of the medical electrical device connector assembly.

32. The electrical contact of claim 31, wherein:
the first portion of the electrical coupling receptacle is formed by first and second opposing sidewalls;
the second portion of the electrical coupling receptacle is formed by third and fourth opposing sidewalls; and
the first and second sidewalls are spaced apart from the third and fourth sidewalls along the longitudinal axis.

33. The electrical contact of claim 31, wherein the first portion of the electrical coupling receptacle includes a first pair of opposing contact surfaces and a second pair of opposing contact surfaces, the first pair of opposing contact surfaces being offset from the second pair of opposing contact surfaces in a direction approximately orthogonal to the longitudinal axis; and
the first and second pairs of opposing contact surfaces are adapted to couple with the connector element of the plurality of connector elements mounted on the medical electrical lead connector, when the connector element is received in the first portion.

34. The electrical contact of claim 31, wherein:
the second portion of the electrical coupling receptacle is formed by opposing sidewalls; and
each of the opposing sidewalls includes a first protrusion and a second protrusion, each of the first and second protrusions extending within the coupling receptacle of the contact and being offset from one another in a direction approximately orthogonal to the longitudinal axis, such that the feedthrough member of the device can be fixedly coupled to the second portion of the electrical coupling receptacle between the first and second protrusions of the opposing sidewalls.

35. An electrical contact for a medical electrical device connector assembly, the contact comprising a longitudinal axis and an elongate electrical coupling receptacle, the electrical coupling receptacle including a first portion and a second portion, the first portion and the second portion extending approximately parallel to the longitudinal axis; the first portion being adapted to receive a single connector element of a plurality of connector elements mounted on a connector of a medical electrical lead; and the second portion adapted to receive a feedthrough member of the device; wherein:

the second portion of the electrical coupling receptacle is formed by opposing sidewalls; and each of the opposing sidewalls includes a first protrusion and a second protrusion, each of the first and second protrusions extending within the coupling receptacle of the contact and being offset from one another in a direction approximately orthogonal to the longitudinal axis, such that the feedthrough member of the device can be fixedly coupled to the second portion of the electrical coupling receptacle between the first and second protrusions of the opposing sidewalls.

36. The electrical contact of claim 35, wherein:

the first portion of the electrical coupling receptacle is formed by first and second opposing sidewalls;

the second portion of the electrical coupling receptacle is formed by third and fourth opposing sidewalls; and the first and second sidewalls are spaced apart from the third and fourth sidewalls along the longitudinal axis.

37. An electrical contact for a medical electrical device connector assembly, the contact comprising a longitudinal axis, first and second sidewalls extending continuously along the longitudinal axis and opposite one another, at an angle with respect to one another, to form an electrical coupling receptacle therebetween, a first elongate protrusion extending longitudinally along the first sidewall within an entire length of the electrical coupling receptacle, and a second elongate protrusion extending longitudinally along the second sidewall within an entire length of the electrical coupling receptacle; wherein, the electrical coupling receptacle includes a first portion and a second portion, the first portion and the second portion extending approximately parallel to the longitudinal axis, the first portion being adapted to receive a single connector element of a plurality of connector elements mounted on a connector of a medical electrical lead, and the second portion adapted to receive a feedthrough member of the device.

* * * * *